United States Patent [19]

Suares et al.

[11] Patent Number: 5,612,044
[45] Date of Patent: Mar. 18, 1997

[54] SELF-TANNER COSMETIC COMPOSITIONS

[75] Inventors: Alan J. Suares, Cheshire; Brian J. Dobkowski, Milford, both of Conn.

[73] Assignee: Elizabeth Arden Company, Division of Conopco, Inc., New York, N.Y.

[21] Appl. No.: 419,073

[22] Filed: Apr. 7, 1995

Related U.S. Application Data

[62] Division of Ser. No. 808,784, Dec. 16, 1991.

[51] Int. Cl.⁶ .................................. A61K 7/42; A61K 9/66
[52] U.S. Cl. .................... 424/401; 424/59; 424/63; 424/455; 424/492; 424/502; 514/844
[58] Field of Search .................... 424/401, 59, 63, 424/70.12, 70.13, 70.122, 455, 492, 502; 252/174.13; 514/844

[56] References Cited

U.S. PATENT DOCUMENTS

| | | | |
|---|---|---|---|
| 3,809,224 | 5/1974 | Greenwood | 206/47 |
| 3,812,246 | 5/1974 | Vanlerberghe et al. | 424/63 |
| 4,021,538 | 5/1977 | Yu et al. | 424/63 |
| 4,293,543 | 10/1981 | Cotte et al. | 424/59 |
| 4,390,341 | 6/1983 | Jacobs | 424/63 |
| 4,419,343 | 12/1983 | Pauly | 424/60 |
| 4,832,943 | 5/1989 | Grollier et al. | 424/63 |
| 4,839,164 | 6/1989 | Smith | 424/63 |
| 5,089,269 | 2/1992 | Noda et al. | 424/456 |

FOREIGN PATENT DOCUMENTS

| | | |
|---|---|---|
| 61950/90 | 8/1989 | Australia . |
| 1115-014 | 11/1984 | Japan . |

OTHER PUBLICATIONS

Christian Dior phamphelet, "Instant Radiance Relaxing Mask," Feb. 1992, Ref. 39 6164 4000.
J. Soc. Cosmet. Chem., 35—pp. 265–272 (Aug. 1984).
Agric. Biol. Chem. 44(7)—pp. 1595–1599 (1980).

*Primary Examiner*—Thurman K. Page
*Assistant Examiner*—Kathryne E. Shelborne
*Attorney, Agent, or Firm*—Milton L. Honig

[57] ABSTRACT

A cosmetic product and method for imparting a natural-appearing tan to skin is provided, the product being in the form of a multi-compartment dispenser. A first and second substance are stored in separate compartments of the dispenser, at least one of the substances including a silicone. Additionally, the first substance contains an alpha-hydroxy aldehyde such as dihydroxyacetone and the second substance contains at least one amino acid.

10 Claims, No Drawings

SELF-TANNER COSMETIC COMPOSITIONS

This is a divisional application of Ser. No. 07/808,784, filed Dec. 16, 1991, pending.

BACKGROUND OF THE INVENTION

1. Field of the Invention

The invention concerns a cosmetic composition which rapidly imparts a tan similar in color to a natural suntan onto the skin.

2. The Related Art

Today there is a great health concern with natural tanning through sunlight. Ultraviolet radiation from the sun is considered to be a leading factor in causing skin cancer. Even if not lethal, ultraviolet radiation has been acknowledged as accelerating aging and wrinkling processes on the skin.

Beyond health concerns, there are obvious practical reasons against natural tanning. Foremost is the reason that in many areas of the globe and during all but summertime, there is insufficient sunlight available to accomplish a natural tan.

Based on the above considerations, there has been much interest in effectuating a tan through cosmetic means. Dihydroxyacetone (hereinafter known as DHA) has widely been utilized in cosmetics to accomplish self-tanning of the skin. In the *J. Soc. Cosmet. Chem.*, 35, pages 265–272 (August 1984), Bobin et al. studied the Maillard reaction of DHA with various amino acids found naturally in the hydrolipid film and first layers of the stratum cornsum. The Maillard reaction method has commonly been utilized as an artificial tanning system since 1960. As a reference standard, Bobin et al. evaluated a mixture of amino acids thought normally to be found in the stratum corneum. This amino acid mixture included L-serine 24.7%, L-citrulline 16.4%, L-glycine 9.3%, L-alanine 8.9%, L-threonine 7.7%, L-aspartic Ac.5.5%, L-arginine 4%, L-histidine 3.6%, L-lysine 3.4%, L-tyrosine 3.2%, L-leucine 3%, L-valine 2.5%, L-glutamic Ac. 2.3%, L-phenylalanine 2.3%, L-proline 1.9% and L-ornithine 1.3%. Methionine sulfoxide was found to be the best amino acid or derivative in combination with DHA. It was suggested that these substances be separately formulated maintaining them apart in a compartmented dispensing device until use. Optical density results presented in the Bobin et al. article indicated that a full tanning color was not obtained until the passage of 72 hours. Even the use of isolated amino acids as opposed to the natural mixture did not improve the speed of coloration.

Other studies on the Maillard reaction between DHA and amino acids have been reported in *Agric. Biol. Chem.*, 44 (7), pages 1595–1599 (Kawashima et al.). Through this study it was determined that the rate of browning was maximum around a DHA-amino acid molar ratio of 1.5 when the total concentration of both reactants together was constant at 0.1M. Lysine and glycine were found to have the highest browning activity.

Another approach to the tanning problem is reported in Australian Patent 61950/90 to L'Oreal. The art had earlier appreciated that both DHA and 5,6-dihydroxy indole and certain of its derivatives would each independently cause coloration in the skin; the mechanisms were each believed to be different. The Australian patent teaches that a combination of these materials achieves a rapidly developed intense coloration much closer to the hue imparted by natural tanning than the colorations obtained with each of the compounds taken separately. Since DHA and indole are unstable in the presence of one another, the patent further suggested delivering these compounds from separate compartments of a multi-compartment kit.

Although there has been great progress in self-tanning compositions as noted above, considerable further progress is needed to increase speed of coloration and achieve a coloration even closer to a natural tan. For medical safety reasons, it is also preferred to avoid use of indoles.

Accordingly, it is an object of the present invention to provide a method and composition for self-tanning having improved rates of coloration and imparting a more natural hue.

A further object of the present invention to provide a method and composition for self-tanning which utilizes ingredients that impart good aesthetics and have an impeccable health safety profile.

These and other objects of the present invention will become more readily apparent through the following summary, detailed discussion and Examples which follow.

SUMMARY OF THE INVENTION

A method is provided for imparting a natural-appearing tan to skin comprising the steps of:

(i) delivering from separate compartments of a multi-compartment dispenser a first and second substance, at least one of the substances including from about 0.1 to about 60% of a silicone, the first substance comprising:

from about 0.1 to about 40% of a $C_3$–$C_{24}$ alpha-hydroxy aldehyde; and an effective amount of a pharmaceutically acceptable vehicle for delivering the alpha-hydroxy aldehyde; and the second substance comprising: from about 0.01 to about 25% of at least one amino acid; and an effective amount of a pharmaceutically acceptable vehicle for delivering the at least one amino acid; and (ii) spreading on the skin a combination of the first and second substances delivered from the dispenser.

Also provided is a cosmetic product in the form of a multi-compartment dispenser wherein a first and second substance are stored in separate compartments thereof, at least one of the substances including from about 0.1 to about 60% of a silicone, the first substance comprising:

from about 0.1 to about 40% of a $C_3$–$C_{24}$ alpha-hydroxy aldehyde; and an effective amount of a pharmaceutically acceptable vehicle for delivering the alpha-hydroxy aldehyde; and the second substance comprising:

from about 0.01 to about 25% of at least one amino acid; and an effective amount of pharmaceutically acceptable vehicle for delivering the at least one amino acid.

DETAILED DESCRIPTION OF THE INVENTION

Now it has been discovered that a very rapid self-tanning can be accomplished by delivering to the skin an alpha-hydroxy aldehyde, a silicone and one or more amino acids. The preferred amino acids are those of glycine, lysine, ornithine, tryptophan and mixtures thereof. Further, it is important that the aldehyde and amino acids be stored in separate compartments, preferably within separate compartments of the same multi-compartment dispenser. A still further aspect of the invention has been the discovery that silicones can positively influence the intensity of the tan.

A first substance or phase according to the invention will comprise a $C_3$–$C_{24}$ alpha-hydroxy aldehyde in an amount from about 0.1 to about 40%, preferably from about 1 to about 20%, optimally between about 2 and 15% by weight. The alpha-hydroxy aldehyde may be selected from dihydroxyacetone, glucose, xylose, fructose, reose, ribose, pentose, arabinose, allose, tallose, altrose, mannose, galactose, lactose, sucrose, erythrose, glyceraldehyde and combinations thereof. Most preferred is dihydroxyacetone.

Amino acids are formulated in a second substance or phase. Glycine is the most preferred of the amino acids for purposes of this invention. Optionally, lysine and/or ornithine may be included along with the glycine. Especially effective is a combination of glycine, lysine and ornithine with the ratio of glycine to a combination of lysine and ornithine being from 50:1 to 1:2, optimally from 20:1 to 10:1; the ratio of lysine to ornithine can range from 10:1 to 1:10. Levels of each of the amino acids may range from about 0.01 to about 25%, preferably from about 0.1 to about 7%, optimally between about 0.5 and 5% by weight.

While dyes such as indole derivatives may be incorporated into either of the components or phases, for health and performance reasons, it may be desirable to formulate in the absence of indole derivatives.

The weight ratio of the first to second substance may range from about 10:1 to 1:10, preferably 2:1 to 1:2, optimally about 1:1. In a preferred embodiment, both the first and second phases have essentially identical components (or at least 90% by weight thereof identical) except for the aldehyde and amino acids being kept in separate phases.

Importantly, compositions of the present invention will contain certain types of silicone oils. Silicone oils may be divided into the volatile and nonvolatile variety. Both types of silicone oils, but especially volatile silicone oils, unexpectedly have displayed a positive interaction with alpha-hydroxy aldehyde and amino acids to enhance the coloration. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms.

Linear volatile silicone materials generally have viscosities less than about 5 centistokes at 25° C. while cyclic materials typically have viscosities of less than about 10 centistokes.

Examples of preferred volatile silicone oils useful herein include: Dow Corning 344, Dow Corning 345 and Dow Corning 200 (manufactured by Dow Corning Corp.); Silicone 7207 and Silicone 7158 (manufactured by the Union Carbide Corp.); SF 1202 (manufactured by General Electric); and SWS-03314 (manufactured by SWS Silicones, Inc.).

The nonvolatile silicone oils useful in compositions of this invention are exemplified by the polyalkyl siloxanes, polyalklyaryl siloxanes and polyether siloxane copolymers. The essentially nonvolatile polyalkyl siloxanes useful herein include, for example, polydimethyl siloxanes with viscosities of from about 5 to about 100,000 centistokes at 25° C. Among the preferred nonvolatile silicones useful in the present compositions are the polydimethyl siloxanes having viscosities from about 10 to about 400 centistokes at 25° C. Such polyalkyl siloxanes include the Viscasil series (sold by General Electric Company) and the Dow Corning 200 series (sold by Dow Corning Corporation). Polyalkylaryl siloxanes include poly(methylphenyl)siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is available as SF-1066 organosilicone surfactant (sold by General Electric Company). Cetyl dimethicone copolyol and cetyl dimethicone are especially preferred because these materials also function as emulsifiers and emollients.

For purposes of the present invention, silicones may be present in amounts ranging from about 0.1 up to about 60%, preferably from about 2 to about 25%, optimally between about 10 and 20% by weight. The relative weight ratio of silicone to total amino acid will range from about 50:1 to 1:10, preferably from about 20:1 to 1:8, optimally from about 10:1 to 1:5.

Synthetic esters are a further category of possible components utilized as emollients which may be included within compositions of the invention. Among the ester emollients are:

(1) Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate. Particularly preferred are $C_{12}$–$C_{15}$ alcohol benzoate esters.

(2) Alkenyl esters of fatty acids having 10 to 20 carbon atoms. Examples thereof include oleyl myristate, oleyl stearate, and oleyl oleate.

(3) Ether-esters such as fatty acid esters of ethoxylated fatty alcohols.

(4) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(5) Wax esters such as beeswax, spermaceti, myristyl myristate, stearyl stearate.

(6) Sterols esters, of which cholesterol fatty acid esters are examples thereof.

Humectants of the polyhydric alcohol-type may also be included in the compositions of this invention. The humectant aids in increasing the effectiveness of the emollient, reduces scaling, stimulates removal of built-up scale and improves skin feel. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. Propylene glycol is especially preferred for use in the amino acid phase. The amount of humectant may range anywhere from 0.1 to 20%, preferably between 0.5 and 5% by weight of the composition.

The compositions of the invention can also include thickeners/viscosifiers in amounts up to about 10% by weight. As known to those skilled in the art, the precise amount of thickeners can vary depending upon the desired consistency and thickness of the composition. Especially preferred is trihydroxystearin. Other exemplary thickeners are xanthan gum, sodium carboxymethyl cellulose, hydroxyalkyl and alkyl celluloses, and cross-linked acrylic acid polymers such as those sold by B.F. Goodrich under the Carbopol trademark.

Compositions of the present invention may also include emulsifiers or surfactants which may be of the nonionic, anionic, cationic or amphoteric type. Examples of satisfactory nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono and di-fatty acid esters of ethylene glycol wherein the fatty acid moiety contains from 10 to 20 carbon atoms, fatty acid monoglyceride wherein the fatty acid moiety contains from 10 to 20 carbon atoms, polyoxyethylene sorbitol, polyoxypropylene sorbitan, and hydrophilic wax esters. Amounts of the emulsifier may range anywhere from about 0.1 to about 20% by weight of the composition, preferably from about 2 to about 10% by weight.

Water is a preferred carrier for the compositions of this invention. The amount of water may range from about 10 to about 95%, preferably from about 30 to about 80%, optimally between about 40 and 60% by weight.

Contemplated within the scope of this invention are water-in-oil emulsions in the form of lotions and creams. Oil advantageously is the continuous phase. The amounts of the oil to water phases may range from about 2:1 to 1:100, preferably about 1:1 to 1:10.

Among other skin benefit agents which may be present in the compositions of this invention are fatty acids and alcohols having from 10 to 20 carbon atoms. Suitable examples of the fatty acids include pelargonic, lauric, myristic, palmitic, stearic, isostearic, hydroxystearic, oleic, linoleic, ricinoleic, arachidic, behenic, and erucic acids. Examples of satisfactory fatty alcohols include lauryl, myristyl, cetyl, hexadecyl, stearyl, isostearyl, hydroxystearyl, oleyl, ricinoleyl, behenyl, erucyl, and 2-octyl dodecanyl alcohols. These materials may be present in amounts anywhere from about 0.1 to about 20% by weight of the composition.

Preservatives can desirably be incorporated into the cosmetic compositions of this invention to protect against the growth of potentially harmful microorganisms. While it is in the aqueous phase that microorganisms tend to grow, microorganisms can also reside in the oil phase. As such, preservatives which have solubility in both water and oil are preferably employed in the present compositions. Suitable traditional preservatives for compositions of this invention are alkyl esters of parahydroxy-benzoic acid. Other preservatives which have more recently come into use include hydantoin derivatives, proprionate salts, and a variety of quaternary ammonium compounds. Cosmetic chemists are familiar with appropriate preservatives and routinely choose them to satisfy the preservative challenge test and to provide product stability. Particularly preferred preservatives are methylparaben, imidazolidinyl urea, sodium dehydroxyacetate, propylparaben, trisodium ethylenediamine tetraacetate (EDTA) and benzyl alcohol. The preservative should be selected having regard for possible incompatibilities between the presevative and other ingredients. Preservatives are preferably employed in amounts ranging from about 0.01% to about 2% by weight of the composition.

Minor adjunct ingredients may also include fragrances, antifoam agents, opacifiers (e.g. titanium dioxide) and colorants, each in their effective amounts to accomplish their respective functions. Particularly useful minor ingredients are vitamin E linoleate, sodium hyaluronate and aloe vera gel, as well as other botanicals.

A sunscreen agent is a further desirable ingredient of the compositions of this invention. This ingredient is preferably incorporated into the second component or oily phase. The term "sunscreen agent" as used herein defines ultraviolet ray-blocking compounds exhibiting absorption within the wavelength region between 290 and 400 nm. Sunscreens may be classified into five groups based upon their chemical structure: para-amino benzoates; salicylates; cinnamates; benzophenones; and miscellaneous chemicals including menthyl anthralinate and digalloyl trioleate. Inorganic sunscreens may also be used including titanium dioxide, zinc oxide, iron oxide and polymer particles such as those of polyethylene and polyamides. Preferred materials include p-aminobenzoic acid and its derivatives, anthralinates; salicylates; cinnamates; courmarin derivatives; azoles; and tannic acid and its derivatives. Among FDA approved sunscreens are those listed in the table below.

|  | Approved % |
|---|---|
| UV-A Absorbers | |
| Oxybenzone, also known as 2-hydroxy-4-methoxy benzophenone, and benzophenone-3, available as Uvinul M-40 and Gafsorb 2H4M | 2–6 |
| Dioxybenzone, also known as 2,2 dihydroxy-4-methoxy benzophenone, and benzophenone-8 | 3 |
| Sulibenzone, also known as 2-hydroxy-4-methoxy benzophenone-5-sulphonic acid, and benzophenone-4, available as Uvinul MS-40 and Gafsorb 2H4MS | 5–10 |
| Menthyl anthralinate, also known as menthyl-o-aminobenzoate | 3.5–5 |
| UV-B Absorbers | |
| p-Amino benzoic acid, also known as PABA | 5–15 |
| Amyl dimethyl PARA (NA), also known as amyl-p-dimethyl ammonium benzoate, available as Padimate A | 1–5 |
| 2-Ethoxy ethyl p-methoxy cinnamate (NA), available as Cinoxate and Givtan-F | 1–3 |
| Diethanolanine p-ethoxy cinnamate, also known as DEA methoxy cinnamate, available as Parsol-Hydro | 8–10 |
| Digalloyl trioleate (NA), a component of Solprotex I | 2–5 |
| Ethyl-4-bis (hydroxypropyl) aminobenzoate, also known as ethyl dihydroxy propyl PABA, available as Amerscreen P | 1–5 |
| 2-Ethyl hexyl-2-cyano-3,3 diphenyl acrylate, also known as octocrylene and available as Uvinul N-539 | 7–10 |
| Ethyl hexyl p-methoxy cinnamate, also known as octyl methoxycinnamate available as Parsol MCX | 2–7.5 |
| 2-Ethyl hexyl salicylate, also known as octyl salicylate | 3–5 |
| Glyceryl aminobenzoate, also known as glyceryl p-aminobenzoate and glyceryl PABA, available as Escalol 106 | 2–3 |
| Homomenthyl salicylate, also known as 3,3,5-trimethylcyclohexyl salicylate | 4–15 |
| Lawsone with dihydroxyacetone (NA) | 0.25 with 33 |
| Octyl dimethyl PABA, also known as 2-ethyl hexyl p-dimethyl p-aminobenzoate, and 2-ethyl hexyl dimethyl PABA, available as Padimate O and Escalol 507 | 1.4–8 |
| 2-Phenyl benzimidazole 5-sulphoic acid | 1.4 |
| Triethanolamine salicylate | 5–12 |
| Physical Screens | |
| Red Petrolatum | 30–100 |
| Titanium dioxide | 2–25 |

According to the present invention there is required a multi-compartment dispenser. Illustrative of such dispensers are those described in U.S. Pat. Nos. 1,639,699 and 1,699,532, each to Hopkins, describing double collapsible tubes. Separation of reactive components is also described in U.S. Pat. No. 4,211,341 (Weyn). Other examples are those found in U.S. Pat. No. 4,487,757 (Kiozpeoplou) in FIG. 1 as well as U.S. Pat. No. 4,528,180, U.S Pat. No. 4,687,663 and U.S. Pat. No. 4,849,213, each of which is to Schaeffer.

Most preferred for purposes of this invention is a dual container tube described in copending U.S. patent application Ser. No. 07/686,730 filed Apr. 17, 1991. Each of a pair of compartments in the dual container described therein is flexible walled and received in a relatively rigid receptacle having a left and right wall positioned on opposite sides of the receptacle. Within each of the latter walls are a respective window through which a button protrudes that, when squeezed, compresses the respective compartments and forces a composition to exit therefrom.

The term "multi-compartment" also includes separation by means of encapsulation. Thus, cosmetic compositions of this invention, such as water-in-oil emulsions, may contain microcapsules surrounding an amino acid core, an alpha-hydroxy aldehyde core or both types of microcapsules, the capsule walls serving as a separating compartment. Release of amino acids and/or aldehydes occurs by crushing of the capsule walls as the product is rubbed onto the skin.

The following examples will more fully illustrate the embodiments of this invention. All parts, percentages and proportions referred to herein and in the appended claims are by weight unless otherwise indicated.

EXAMPLE 1

In vitro studies were conducted for a self-tanning two-phase system. Color development was measured by spectrophotometry with focus upon the wavelength at 420 nm. Reaction between the first and second substances containing DHA and an amino acid, respectively, were conducted at 37° C. utilizing 0.01M amino acid and 2M DHA aqueous solutions. Each solution was buffered with 39% sodium dihydrogen phosphate hydrate and 61% disodium hydrogen phosphate heptahydrate. These solutions were formulated to 100 ml each. A Perkin-Elmer 559UV-VIS Spectrophotometer was employed to measure the absorbance at 420 nm color evolution as a function of time. Results are recorded in Table I.

EXAMPLE 2

A first and second phase formulation according to the present invention was prepared with each phase being stored in a separate compartment in a dual-compartment dispenser. Table II lists the components of each phase.

TABLE II

| Ingredient | Wt. % |
| --- | --- |
| DHA Phase | |
| Dihydroxy Acetone | 14.00 |
| Cyclomethicone | 10.00 |
| Octyl Methoxycinnamate | 7.50 |
| Benzophenone-3 | 2.00 |
| Polyglyceryl Ricinoleate | 2.00 |
| Cetyl Dimethicone Copolyol | 1.00 |
| Sodium Chloride | 1.00 |
| Preservatives | 0.40 |
| Deionized Water | Balance |
| Amino Acid Phase | |
| Cyclomethicone | 10.00 |
| Octyl Methoxycinnamate | 7.50 |
| Glycine | 3.40 |
| Benzophenone-3 | 2.00 |
| Polyglyceryl Ricinoleate | 2.00 |
| Cetyl Dimethicone Copolyol | 1.00 |
| Sodium Chloride | 1.00 |
| Preservatives | 0.40 |
| Lysine Hydrochloride | 0.10 |
| Ornithine Hydrochloride | 0.10 |
| Deionized Water | Balance |

The formulation according to Table II is dispensed by extruding equal amounts of the DHA and amino acid phases from their respective compartments onto human skin. These phases are then intimately mixed together and rubbed into the skin. Within only a few hours, an almost natural tan arises.

TABLE I

| Amino Acid | Molecular Weight | Grams Used in 0.01 M Amino Acid | Grams of DHA Used for 0.2 M | Optical Density | | |
| --- | --- | --- | --- | --- | --- | --- |
| | | | | 24 Hours | 48 Hours | 72 Hours |
| Lysine | 182.65 | .1826 | 3.6032 | .158 | .318 | .489 |
| Glycine | 77.05 | .0770 | 3.6032 | .179 | .249 | .311 |
| Tyrosine | 181.09 | .1811 | 3.6032 | NOT SOLUBLE | | |
| Arginine | 174.20 | .1742 | 3.6032 | .083 | .160 | .222 |
| Isoleucine | 131.18 | .1312 | 3.6032 | .056 | .134 | .186 |
| Citroleucine | 175.19 | .1752 | 3.6032 | .082 | .150 | .238 |
| Aspartic Acid | 133.10 | .1331 | 3.6032 | .059 | .130 | .189 |
| Threonine | 119.12 | .1191 | 3.6032 | .026 | .070 | .042 |
| Aspargine.H$_2$O | 150.14 | .1501 | 3.6032 | .082 | .160 | .210 |
| Histadine HCl | 191.16 | .1912 | 3.6032 | .056 | .084 | .115 |
| Alanine | 89.09 | .0891 | 3.6032 | .116 | .183 | .246 |
| Leucine | 131.18 | .1312 | 3.6032 | .110 | .186 | .243 |
| Cysteine | 121.16 | .1212 | 3.6032 | .018 | .040 | .010 |
| Tryptophan | 201.23 | .2042 | 3.6032 | .159 | .324 | .592 |
| Cystine | 204.30 | .2043 | 3.6032 | NOT SOLUBLE | | |
| Glutamine | 146.15 | .1461 | 3.6032 | .108 | .192 | .237 |
| Ornithine.HCl | 168.42 | .1686 | 3.6032 | .332 | .412 | .483 |
| Methionine | 149.21 | .1492 | 3.6032 | .110 | .192 | .267 |
| Proline | 115.13 | .1151 | 3.6032 | .007 | .029 | .043 |
| Histidine | 155.16 | .1552 | 3.6032 | .061 | .094 | .189 |
| Serine | 105.09 | .1051 | 3.6032 | .021 | .055 | .089 |
| Arginine.HCl | 174.20 | .1742 | 3.6032 | .099 | .186 | .257 |

From Table I it is evident that the fastest reacting amino acid is tryptophan. Other amino acids providing good color intensity were glycine, lysine and ornithine.

EXAMPLE 3

This Example illustrates the affect of the relative weight ratio between cyclomethicone (silicone) and the total amount of amino acids. Table III correlates the ratios with intensity and color change. Intensity is indicated by the "+" symbol, the greatest intensity being symbolized as "+++". Observations were taken at 3 hours and at 24 hours. Seven panelists participated in these trials. Each of the three test creams were simultaneously applied to the forearm of the panelist with a dosage of 3.92 mg/cm$^2$. The panelists were allowed to shower between the 3 and 24 hour observations. Table IV identifies the formulations used in Table III.

vehicles for the DHA and amino acids. Conditions of the test were similar to that discussed under Example 3. Table V details the results of the experiments. Table VI provides the formulations utilized for these tests.

TABLE III

| | Ratio of Silicone:Amino Acids | | | | | |
|---|---|---|---|---|---|---|
| | 3 Hours | | | 24 Hours | | |
| Panelist No. | 10:1 | 1:1 | 1:10 | 10:1 | 1:1 | 1:10 |
| 1 | +++/red | ++/sl. red | +/yellow | +++/red | +/red | ++/yellow |
| 2 | +++/red | ++/red | +/yellow | +++/red | +/red | ++/yellow |
| 3 | +++/red | ++/red | +++/yellow | +++/red | ++/red | +/yellow |
| 4 | +++/red | ++/red | +/yellow | +++/red | +/red | ++/yellow |
| 5 | +++/red | ++/red | +/yellow | +++/red | ++/red | +/yellow |
| 6 | +++/red | ++/red | +/yellow | +++/red | ++/red | +/yellow |
| 7 | +++/red | ++/red | ++/yellow | +++/red | ++/red | ++/yellow |

TABLE IV

| | 10:1 Ratio | | 1:1 Ratio | | 1:10 Ratio | |
|---|---|---|---|---|---|---|
| Ingredient | A | A' | B | B' | C | C' |
| Deionized water | 66.9 | 56.5 | 83.1 | 72.7 | 84.2 | 74.32 |
| Glycine | 3.4 | — | 3.4 | — | 3.4 | — |
| Lysine.HCl | 0.1 | — | 0.1 | — | 0.1 | — |
| Ornithine.HCl | 0.1 | — | 0.1 | — | 0.1 | — |
| Sodium chloride | 1.0 | 1.0 | 1.0 | 1.0 | 1.0 | 1.0 |
| DHA | — | 14.0 | — | 14.0 | — | 14.0 |
| Cyclomethicone | 18.0 | 18.0 | 1.8 | 1.8 | 0.18 | 0.18 |
| Parsol MCX | 7.5 | 7.5 | 7.5 | 7.5 | 7.5 | 7.5 |
| Octyl Stearate | 7.5 | 7.5 | 7.5 | 7.5 | 7.5 | 7.5 |
| Polyglyceryl ricinoleate | 2.0 | 2.0 | 2.0 | 2.0 | 2.0 | 2.0 |
| Cetyl dimethicone copolyol | 1.0 | 1.0 | 1.0 | 1.0 | 1.0 | 1.0 |

A natural tan is expected to have a reddish rather than a yellow hue. Based on the results listed in Table III, ratios of 10:1 and 1:1 produce the best (i.e. reddish) tan color and provided deepest tan intensity. Where the silicone to amino acid ratio was 1:10, color intensity was generally less and uniformly yellow in hue.

EXAMPLE 4

Experiments hereunder illustrate the effects of emulsion-type on the intensity and color change. A water-in-oil emulsion was compared to an oil-in-water emulsion as

TABLE VI

| | Water-in-Oil Emulsions | | Oil-in-Water Emulsions | |
|---|---|---|---|---|
| Ingredient | A | A' | B | B' |
| Deionized water | 74.9 | 64.5 | 74.9 | 64.5 |
| Sodium chloride | 1.0 | 1.0 | 1.0 | 1.0 |
| Glycine | 3.4 | — | 3.4 | — |
| Lysine.HCl | 0.1 | — | 0.1 | — |
| Ornithine.HCl | 0.1 | — | 0.1 | — |
| DHA | — | 14.0 | — | 14.0 |
| Cyclomethicone | 10.0 | 10.0 | 10.0 | 10.0 |
| Parsol MCX | 7.5 | 7.5 | 7.5 | 7.5 |
| Ceteareth-2 | — | — | 1.0 | 1.0 |
| Ceteareth-21 | — | — | 2.0 | 2.0 |
| Polyglyceryl ricinoleate | 2.0 | 2.0 | — | — |
| Cetyl dimethicone copolyol | 1.0 | 1.0 | — | — |

TABLE V

| | 3 Hours | | 24 Hours | |
|---|---|---|---|---|
| Panelist No. | W/O | O/W | W/O | O/W |
| 1 | +++/redder | +++/yellower | +++/redder | +++/yellower |
| 2 | +++/redder | +/yellower | +++/redder | +(streaky)/yellower |
| 3 | +++/sl. redder | +++/sl. yellower | +++/redder | +++(streaky)/yellower |
| 4 | +++/redder | +(streaky)/yellower | +++/redder | +(streaky)/yellower |
| 5 | +++/sl. redder | +++/sl. yellower | +++/sl. redder | +++/sl. yellower |
| 6 | +++/redder | +/yellower | +++/sl. redder | +++/sl. yellower |
| 7 | +++/redder | +/yellower | +++/redder | +/yellower |

Evident from Table V is that generally the water-in-oil emulsion performed better delivering a more even, redder and somewhat deeper tan color.

EXAMPLE 5

This Example illustrates the affects of varying DHA and amino acid levels. Conditions for the test were identical to those outlined under Example 3. Table VII details the results of these experiments.

TABLE VII

| Wt. % DHA | Wt. % Amino Acids | Ratio DHA:AA | 1 Hour (Color Intensity) |
|---|---|---|---|
| 5.0 | 0 | | + |
| 2.5 | 0.5 | 5:1 | + |
| 2.5 | 3.0 | 1:1.2 | +++ |
| 6.0 | 1.8 | 3.3:1 | +++ |
| 7.0 | 2.3 | 3.0:1 | +++ |
| 7.0 | 1.8 | 3.8:1 | +++ |
| 7.0 | 1.32 | 5.3:1 | +++ |
| 7.5 | 2.0 | 3.7:1 | +++ |
| 8.0 | 3.0 | 2.6:1 | +++ |

From results of Table VII, it is seen that excellent initial color intensity was achieved for a range of concentrations even after only one hour subsequent to treatment.

The following examples illustrate selected embodiments of the present invention and should be considered non-limiting examples with variations and modifications thereof all being within the spirit and purview of this invention.

What is claimed is:

1. A cosmetic product which is a multi-compartment dispenser wherein a first and second substance are stored in separate compartments thereof, at least one of the substances including from about 0.1 to about 60% of a silicone, the first substance comprising:
  from about 0.1 to about 40% of a compound selected from the group consisting of dihydroxy acetone, glucose, xylose, fructose, reose, ribose, pentose, arabinose, allose, tallose, altrose, mannose, galactose, lactose, sucrose, erythrose, glyceraldehyde and combinations thereof; and
  an effective amount of a pharmaceutically acceptable vehicle for supporting the compound; and the second substance comprising:
  from about 0.01 to about 25% of at least one amino acid; and
  an effective amount of a pharmaceutically acceptable vehicle for delivering at least one amino acid.

2. A cosmetic product according to claim 1 wherein the compound is dihydroxy acetone.

3. A cosmetic product according to claim 1 wherein the amino acid is selected from the group consisting of glycine, lysine, ornithine, tryptophan, salts and mixtures thereof.

4. A cosmetic product according to claim 1 wherein the silicone is a cyclic or linear polydimethylsiloxane containing from about 3 to about 9 silicon atoms.

5. A cosmetic product according to claim 1 wherein the silicone and total amino acids present are in a relative weight ratio of from about 50:1 to 1:10.

6. A cosmetic product according to claim 5 wherein the relative weight ratio ranges from about 10:1 to 1:5.

7. A cosmetic product according to claim 1 wherein the first and second substances are water-in-oil emulsions.

8. A cosmetic product according to claim 1 wherein at least one of the substances is encapsulated within a microcapsule, the microcapsule functioning as one of the multi-compartments.

9. A cosmetic product according to claim 1 wherein the silicone and total amino acids present are in a relative weight ratio of from about 10:1 to 1:1.

10. A cosmetic product according to claim 1 wherein the multi-compartment dispenser is a dual container tube with a pair of separate compartments for respectively storing the first and second substance.

\* \* \* \* \*